US009441249B2

(12) United States Patent
Kondo et al.

(10) Patent No.: US 9,441,249 B2
(45) Date of Patent: Sep. 13, 2016

(54) METHOD FOR PRODUCING ETHANOL FROM BIOMASS

(71) Applicant: National University Corporation Kobe University, Hyogo (JP)

(72) Inventors: Akihiko Kondo, Hyogo (JP); Tomohisa Hasunuma, Hyogo (JP); Yuri Sakihama, Hyogo (JP)

(73) Assignee: National University Corporation Kobe University, Hyogo (JP)

( * ) Notice: Subject to any disclaimer, the term of this patent is extended or adjusted under 35 U.S.C. 154(b) by 0 days.

(21) Appl. No.: 14/422,728

(22) PCT Filed: Aug. 23, 2013

(86) PCT No.: PCT/JP2013/072572
§ 371 (c)(1),
(2) Date: Feb. 20, 2015

(87) PCT Pub. No.: WO2014/030745
PCT Pub. Date: Feb. 27, 2014

(65) Prior Publication Data
US 2015/0218592 A1 Aug. 6, 2015

(30) Foreign Application Priority Data

Aug. 24, 2012 (JP) ................. 2012-185913

(51) Int. Cl.
| | |
|---|---|
| C12P 7/06 | (2006.01) |
| C12P 7/10 | (2006.01) |
| C12N 1/00 | (2006.01) |
| C12N 15/00 | (2006.01) |
| C12N 15/74 | (2006.01) |
| C07H 21/02 | (2006.01) |
| C07K 14/395 | (2006.01) |
| C12N 1/14 | (2006.01) |
| C12N 9/16 | (2006.01) |
| C12N 1/16 | (2006.01) |
| C12N 15/81 | (2006.01) |

(52) U.S. Cl.
CPC ............... *C12P 7/06* (2013.01); *C07K 14/395* (2013.01); *C12N 1/14* (2013.01); *C12N 1/16* (2013.01); *C12N 9/16* (2013.01); *C12N 15/815* (2013.01); *C12P 7/10* (2013.01); *Y02E 50/16* (2013.01); *Y02E 50/17* (2013.01); *Y02P 20/52* (2015.11)

(58) Field of Classification Search
None
See application file for complete search history.

(56) References Cited

U.S. PATENT DOCUMENTS

2012/0149081 A1 6/2012 Shisa et al.
2012/0282664 A1 11/2012 Kondo et al.

FOREIGN PATENT DOCUMENTS

JP 2010000024 A 1/2010
JP 2011167096 A 9/2011

OTHER PUBLICATIONS

Chu et al., "Genetic improvement of *Saccharomyces cerevisiae* for xylose fermentation", Biotechnology Advances, vol. 25, 2007, pp. 425-441.
Lu et al., "Shuffling of Promoters for Multiple Genes to Optimize Xylose Fermentation in an Engineered *Sacharomyces cerevisiae* Strain", Applied and Environmental Microbiology, vol. 73, No. 19, Oct. 2007, pp. 6072-6077.
Kuyper et al., "Metabolic engineering of a xylose-isomerase-expressing *Saccharomyces cerevisiae* strain for rapid anaerobic xylose fermentation", FEMS Yeast Research, vol. 5, 2005, pp. 399-409.
Almeida et al., "Increased tolerance and conversion of inhibitors in lignocellulosic hydrolysates by *Saccharomyces cerevisiae*", Journal of Chemical Technology and Biotechnology, vol. 82, 2007, pp. 340-349.
Van Maris et al., "Alcoholic fermentation of carbon sources in biomass bydrolysates by *Saccharomyces cerevisiae*: current status", Antonie van Leeuwenhoek, vol. 90, 2006, 391-418.
Palmqvist et al., "Fermentation of lignocellulosic hydrolysates. II: inhibitors and mechanisms of inhibition", Bioresource Technology, vol. 74, 2000, pp. 25-33.
Gorsich et al., "Tolerance to furfural-induced stress is associated with pentose phosphate pathway genes ZWF1, GND1, RPE1, and TKL1 in *Saccharomyces cerevisiae*", Appl. Microbiol Biotechnol, 2006, vol. 71, pp. 339-349.
Petersson et al., "A 5-hydroxymethyl furfural reducing enzyme encoded by the *Saccharomyces cerevisiae* ADH6 gene conveys HMF tolerance", Yeast, 2006, vol. 23, pp. 455-464.
Bellissimi et al., "Effects of acetic acid on the kinetics of xylose fermentation by an engineered, xylose-isomerase-based *Saccharomyces cerevisiae* strain", FEMS Yeast Res, vol. 9, 2009, pp. 358-364.
Katahira et al., "Ethanol fermentation from lignocellulosic hydrolysate by a recombinant xylose- and cellooligosaccharide-assimilating yeast strain", Appl Microbiol Biotechnol, 2006, vol. 72, pp. 1136-1143.
Mira et al., "Identification of a DNA-binding site for the transcription factor Haa1, required for *Saccharomyces cerevisiae* response to acetic acid stress", Nucleic Acids Research, 2011, vol. 39, No. 16, pp. 6896-6907.

(Continued)

*Primary Examiner* — Iqbal H Chowdhury
(74) *Attorney, Agent, or Firm* — Kilyk & Bowersox, P.L.L.C.

(57) ABSTRACT

Provided is a method for efficiently producing ethanol by ethanol fermentation from xylose using a saccharified biomass, which contains various fermentation inhibitors. A method for producing ethanol from biomass of the present invention includes the step of culturing a xylose-utilizing yeast transformed so as to overexpress a gene for an acetic acid-responsive transcription factor in combination with a saccharified biomass.

6 Claims, 6 Drawing Sheets

(56) References Cited

OTHER PUBLICATIONS

Yamada et al., "Efficient production of ethanol from raw starch by a mated diploid *Saccharomyces cerevisiae* with integrated x-amylase and glucoamylase genes", Enzyme and Microbial Technology, 2009, vol. 44, pp. 344-349.

Fujitomi et al., "Deletion of the PHO13 gene in *Saccharomyces cerevisiae* improves ethanol production from lignocellulosic hydrolysate in the presence of acetic and formic acids, and furfural", Bioresour. Technol., 2012, pp. 1-6.

Ishii et al., "A Simple and Immediate Method for Simultaneously Evaluating Expression Level and Plasmid Maintenance in Yeast", J. Biochem., 2009, vol. 145, pp. 701-708.

Hasunuma et al., "Repeated-batch fermentation of lignocellulosic hydrolysate to ethanol using a hybrid *Saccharomyces cerevisiae* strain metabolically engineered for tolerance to fermentation inhibitors", Abstracts of the Annual Meeting of the Society for Biotechnology, Japan, 2011, vol. 63, p. 113.

Mita et al., "Efficient Production of Bioethanol from Xylose by Acidic Acid Tolerant Yeast", Japan Society for Bioscience, Biotechnology, and Agrochemistry Taikai Koen Yoshishu, 2010, vol. 2010, p. 72.

Fernandes et al., "*Saccharomyces cerevisiae* adaption to weak acids involves the transcription factor Haa1p and Haa1p-regulated genes", Biochemical and Biophysical Research Communications, 2005, vol. 337, pp. 95-103.

Fujitomi et al., "Efficient ethanol production from xylose using *Saccharomyces cerevisiae* mutant deficient in PHO13", Japan Society for Bioscience, Biotechnology, and Agrochemistry Taikai Koen Yoshishu, 2011, vol. 2011, p. 272.

Fujitomi et al., "Deletion of PHO13 gene in a recombinant *Saccharomyces cerevisiae* strain confers tolerance to fermentation inhibitors", Abstracts of the Annual Meeting of the Society for Biotechnology, Japan, 2011, vol. 63, p. 21.

Kuyper et al., "Evolutionary engineering of mixed-sugar utilization by a xylose-fermenting *Saccharomyces cerevisiae* strain", FEMS Yeast Research, vol. 5, 2005, pp. 925-934.

International Search Report issued in corresponding International Patent Application No. PCT/JP2013/072572 dated Sep. 17, 2013 (2 pages).

IPRP issued in corresponding International Patent Application No. PCT/JP2013/072572 dated Jul. 1, 2014 in Japanese with English translation (13 pages).

(A)

(B)

(C)

(D)

(E)

(F)

(A)

(B)

(A)

(B)

(A)

(B)

METHOD FOR PRODUCING ETHANOL FROM BIOMASS

The present application is a National Stage Application of PCT/JP2013/072572, filed Aug. 23, 2013, which claims priority from Japanese Patent Application No. 2012-185913, filed Aug. 24, 2012.

TECHNICAL FIELD

The present invention relates to a method for producing ethanol from biomass

BACKGROUND ART

With a concern about depletion for fossil fuels, alternative fuels are now being developed. In particular, bioethanol derived from biomass is focused because biomass is a renewable resource which occurs in great abundance on earth, and can be used without increasing carbon dioxide in the atmosphere (carbon neutral) to contribute to prevention of global warming.

However, currently, mainly corn and sugar cane are used as raw materials to produce bioethanol, which causes competition with food. Therefore, it is desired in the future to produce bioethanol using lignocellulose-based biomass, such as rice straw, straw, and wood scrap, as a raw material to avoid the competition with food.

Lignocellulose-based biomass is composed mainly of three components, cellulose, hemicellulose, and lignin. Among these, cellulose can be converted to glucose by saccharification, and then used in ethanol fermentation by a glucose-utilizing yeast such as *Saccharomyces cerevisiae* or the like. In contrast, hemicellulose can be converted to a pentose such as xylose or arabinose by saccharification, but is hardly used in ethanol production by fermentation in that naturally-occurring yeasts have a very poor ability to utilize xylose or arabinose.

Accordingly, for xylose utilization, a yeast has been genetically engineered to overexpress xylose reductase (XR) and xylitol dehydrogenase (XDH) derived from the yeast *Pichia stipitis* and xylulokinase (XK) derived from the yeast *Saccharomyces cerevisiae* by introducing the genes for these enzymes into the yeast (Non-Patent Documents 1 and 2). In addition, a yeast that allows ethanol fermentation from xylose has been made by introducing genes for xylose isomerase (XI) derived from anaerobic fungus *Piromyces* or *Orpinomyces* and XK derived from the yeast *Saccharomyces cerevisiae* into the yeast to express them (Non-Patent Document 3).

Thus, ethanol fermentation from xylose has been made possible by the creation of such xylose-utilizing yeasts. However, there are various problems with developing ethanol fermentation from xylose to an industrial scale, including, for example, a lower utilization (consumption) rate, a lower ethanol production rate, and a lower ethanol yield with xylose than with glucose; and the presence of fermentation inhibitors in a saccharified biomass, which is the problem to be mostly solved for putting ethanol production from cellulose-based biomass into practical use.

Cellulose-based biomass can be degraded (saccharified) to C6 sugar such as glucose, or C5 sugar such as xylose or arabinose using the process such as enzymatic treatment, treatment with diluted sulfuric acid, or hydrothermal treatment. According to enzymatic treatment, enzymes are required in a large variety and amount, which causes the problem of cost with the development to an industrial scale; while according to treatment with diluted sulfuric acid or hydrothermal treatment, various overdegraded products (by-products) may occur, including weak acids such as acetic acid and formic acid; aldehydes such as furfural and hydroxymethylfurfural (HMO; and phenols including vanillin, and it has been known that such by-products are fermentation inhibitors which greatly inhibit ethanol fermentation from xylose (Non-Patent Documents 4 to 6). Therefore, a yeast that is tolerant to overdegraded products of biomass, or a yeast that is capable of efficient ethanol fermentation even in the presence of such fermentation inhibitors is desired so that cost-effective procedures, treatment with sulfuric acid and hydrothermal treatment can be used to put ethanol fermentation from biomass into practical use.

Heretofore, the influence of fermentation inhibitors on yeasts has been investigated (Non-Patent Documents 4 to 6). It has been found that furfural has a great influence on the survival, growth rate, budding, ethanol yield, biomass yield, and enzymatic activity of yeasts. It has been found that HMF causes accumulation of lipids, reduces the protein content, and inhibits alcohol dehydrogenase, aldehyde dehydrogenase, and pyruvate dehydrogenase in yeast cells. Research has been carried out using screening of disrupted strains or transcriptional analysis to search for a gene tolerant to furfural or HMF (Non-Patent Documents 7 and 8).

Meanwhile, it was thought that weak acids such as acetic acid and formic acid would affect the pH in yeast cells, in other words, weak acids would occur in the medium in an undissociated form, and the undissociated weak acid would penetrate through the cell membrane of yeast into the cytosol of the yeast with around neutral pH, and then become dissociated into an anion and a proton to cause pH decrease in the cell of the yeast (Non-Patent Document 4). Then, the pH decrease in the cell would activate ATPase to maintain homeostasis, so requiring ATP. Under anaerobic conditions, ATP is regenerated through ethanol fermentation. It seems that regarding ethanol fermentation from glucose, ATP is generally regenerated even in the presence of acetic acid without affecting the fermentation ability so much; however, regarding ethanol fermentation from xylose, ATP is poorly regenerated in the presence of acetic acid in that the fermenting ability deteriorates.

The inventors have investigated the relation between acetic acid and pH in a fermentation medium using the engineered *Saccharomyces cerevisiae* MN8140X strain into which the genes for XR, XDH, and XK had been introduced, and found that inhibition of fermentation does not occur in this yeast even in the presence of acetic acid when the pH is adjusted from acidic toward neutral. It has been also reported that the same results are obtained in the engineered yeast into which the genes for XI and XK have been introduced (Non-Patent Document 9).

However, the control of pH is not practical to develop ethanol production from cellulose-based biomass to an industrial scale because it is costly and the contamination with other microorganisms may occur with around neutral pH. Accordingly, efficient ethanol fermentation from xylose in the presence of acetic acid (at acidic pH) is desired.

The inventors have conducted a study of efficient ethanol fermentation from xylose even in the presence of acetic acid by the use of a xylose-utilizing yeast transformed so as to overexpress a gene for at least one of pentose phosphate pathway metabolic enzymes such as transaldolase (TAL) and transketolase (TKL) (Patent Document 1).

The inventors have also conducted a study of efficient ethanol fermentation from xylose even in the presence of formic acid by the use of a xylose-utilizing yeast transformed so as to overexpress a gene for formate dehydrogenase (Patent Document 2).

Meanwhile, further improvements in technology are desired that are suited for ethanol fermentation from xylose using an actual saccharified biomass, which contains various fermentation inhibitors.

PRIOR ART DOCUMENTS

Patent Documents

Patent Document 1: WO 2011/065539
Patent Document 2: Japanese Laid-Open Patent Publication No. 2011-167096

Non-Patent Documents

Non-Patent Document 1: B. C. H. Chu and H. Lee, "Genetic improvement of *Saccharomyces cerevisiae* for xylose fermentation", Biotechnology Advances, 2007, vol. 25, pp. 425-441
Non-Patent Document 2: C. Lu and T. Jeffries, "Shuffling of promoters for multiple genes to optimize xylose fermentation in an engineered *Saccharomyces cerevisiae* strain", Appl. Environ. Microbiol., 2007, vol. 73, pp. 6072-6077
Non-Patent Document 3: M. Kuyper et al., "Metabolic engineering of a xylose-isomerase-expressing *Saccharomyces cerevisiae* strain for rapid anaerobic xylose fermentation", FEMS Yeast Res., 2005, vol. 5, pp. 399-409
Non-Patent Document 4: J. R. M. Almeida et at, "Increased tolerance and conversion of inhibitors in lignocellulosic hydrolysates by *Saccharomyces cerevisiae*", J. Chem. Technol. Biotechnol., 2007, vol. 82, pp. 340-349
Non-Patent Document 5: A. J. A. van Maris et al., "Alcoholic fermentation of carbon sources in biomass hydrolysates by *Saccharomyces cerevisiae*: current status", Antonie van Leeusenhoek, 2006, vol. 90, pp. 391-418
Non-Patent Document 6: E. Palmqvist and B. Hahn-Hagerdal, "Fermentation of lignocellulosic hydrolysates. II: inhibitors and mechanisms of inhibition", Bioresource Technology, 2000, vol. 74, pp. 25-33
Non-Patent Document 7: S. W. Gorsich et al., "Tolerance to furfural-induced stress is associated with pentose phosphate pathway genes ZWF1, GND1, RPE1, and TKL1 in *Saccharomyces cerevisiae*", Appl. Microbiol. Biotechnol., 2006, vol. 71, pp. 339-349
Non-Patent Document 8: A. Petersson et at, "A 5-hydroxymethyl furfural reducing enzyme encoded by the *Saccharomyces cerevisiae* ADH6 gene conveys HMF tolerance", Yeast, 2006, vol. 23, pp. 455-464
Non-Patent Document 9: E. Bellissimi et al., "Effects of acetic acid on the kinetics of xylose fermentation by an engineered, xylose-isomerase-based *Saccharomyces cerevisiae* strain", FEMS Yeast Res., 2009, vol. 9, pp. 358-364

SUMMARY OF INVENTION

Problems to be Solved by the Invention

An object of the present invention is to provide a method for efficiently producing ethanol by ethanol fermentation from xylose using a saccharified biomass, which contains various fermentation inhibitors.

Means for Solving the Problems

In order to solve the above-described problems, the inventors have found that a transformed yeast overexpressing a gene for an acetic acid-responsive transcription factor, the yeast being obtained by introducing that gene into a xylose-utilizing yeast, is tolerant to various fermentation inhibitors in a saccharified biomass, and thus accomplished the present invention.

The present invention provides a method for producing ethanol from biomass, the method including the step of culturing a xylose-utilizing yeast transformed so as to overexpress a gene for an acetic acid-responsive transcription factor in combination with a saccharified biomass.

In one embodiment, the acetic acid-responsive transcription factor is Haa1.

In one embodiment, the transformed xylose-utilizing yeast is deficient in a PHO13 gene.

In one embodiment, the saccharified biomass contains a fermentation inhibitor.

In one embodiment, the fermentation inhibitor is at least one selected from the group consisting of acetic acid, formic acid, furfural, hydroxymethylfurfural, and vanillin.

The present invention also provides a xylose-utilizing yeast that is transformed so as to overexpress a gene for an acetic acid-responsive transcription factor.

In one embodiment, the acetic acid-responsive transcription factor is Haa1.

In one embodiment, the transformed xylose-utilizing yeast is deficient in a PHO13 gene.

Moreover, the present invention provides a method for producing a xylose-utilizing yeast that exhibits tolerance to a fermentation inhibitor when being cultured and fermented in combination with a saccharified biomass, the method including the step of transforming a xylose-utilizing yeast so that the xylose-utilizing yeast overexpresses a gene for an acetic acid-responsive transcription factor. Furthermore, the present invention provides a method for producing a xylose-utilizing yeast that exhibits tolerance to acetic acid when being cultured and fermented in combination with a saccharified biomass, the method including the step of transforming a xylose-utilizing yeast so that the xylose-utilizing yeast overexpresses a gene for an acetic acid-responsive transcription factor.

In one embodiment, the acetic acid-responsive transcription factor is Haa1.

In one embodiment, the method further includes the step of making the xylose-utilizing yeast deficient in a PHO13 gene.

Effects of Invention

According to the method of the present invention, ethanol can be efficiently produced by ethanol fermentation from xylose using a saccharified biomass, which contains various fermentation inhibitors. It is thus possible to produce bioethanol using lignocellulose-based biomass, such as rice straw, straw, and wood scrap, as a raw material to avoid the competition with food.

MODE FOR CARRYING OUT THE INVENTION

Yeast of the Present Invention

Figure 1:
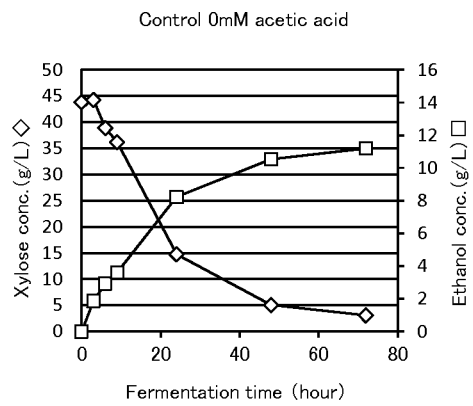
FIG. 1 represents graphs showing changes over time in the concentrations of the substrate (xylose) and the product (ethanol) in the fermentation liquid with respect to strains pRS425pTDH3/Haa1 (Haa1-overexpressing strain, D to F) and pRS425pTDH3 (control strain, A to C) where ethanol fermentation from xylose is performed in the absence of acetic acid (0 mM: A and D) and in the presence of acetic acid (30 mM: B and E, and 60 mM: C and F).
Figure 1:
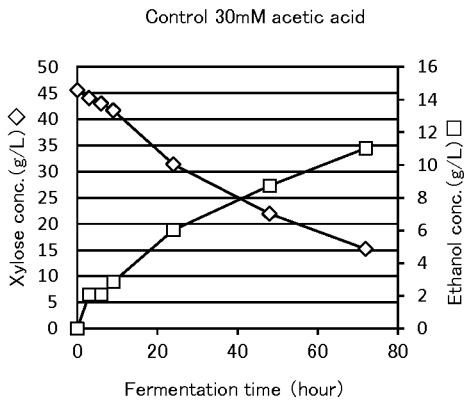
Figure 1:
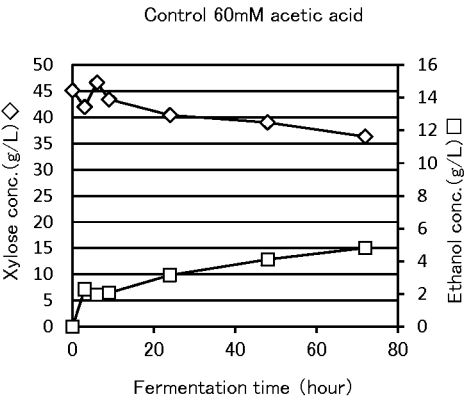
Figure 1:
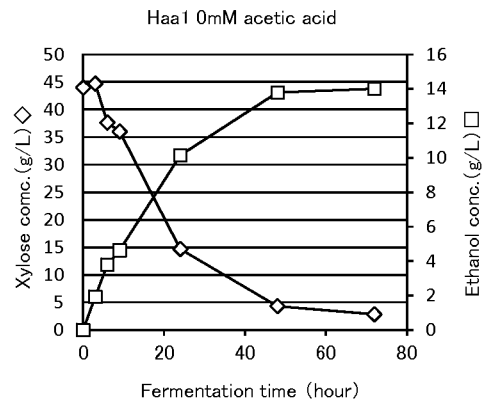
Figure 1:
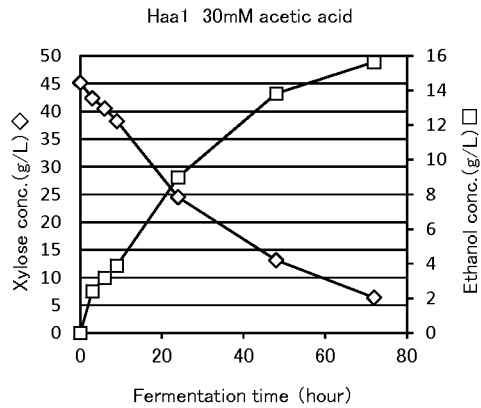
Figure 1:
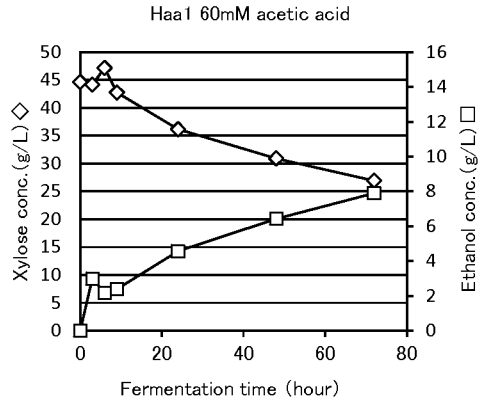

The yeast according to the present invention is a transformed xylose-utilizing yeast into which a gene for an acetic acid-responsive transcription factor has been introduced. The xylose-utilizing yeast to be used for transformation is not particularly limited as long as it is any yeast that can produce ethanol from xylose through ethanol fermentation, including a xylose-utilizing yeast obtained by introducing into the yeast *Saccharomyces cerevisiae* a plasmid for imparting a xylose-utilizing ability, which can be prepared, for example, as described in S. Katahira et al., Appl. Microbiol. Biotechnol., 2006, vol. 72, pp. 1136-1143.

The procedure for introducing a gene into a yeast is not particularly limited, and examples thereof include lithium acetate treatment, electroporation, and protoplast. The gene introduced may be present in the form of a plasmid, or may be present in the form in which the gene is inserted into the chromosome of the yeast or in the form in which the gene is integrated in the yeast chromosome by homologous recombination.

An example of the acetic acid-responsive transcription factor is, but not particularly limited to, Haa1. Preferably, Haa1 is used. It is known that Haa1 (E. Bellissimi et at, "Identification of a DNA-binding site for the transcription factor Haa1, required for *Saccharomyces cerevisiae* response to acetic acid stress", Nucleic Acids Res., 2011, vol. 39, pp. 6896-6907), in response to acetic acid, activates expression of the TPO2 gene, the YLR297w gene, the STP3 gene, the YRO2 gene, the YAR029w gene, the TOS3 gene, the YIR035c gene, the YGP1 gene, the PCL10 gene, the YPR127w gene, the DSD1 gene, the MSN4 gene, the YJR096w gene, the SPI1 gene, the HOR2 gene, the YKR075c gene, the SUR2 gene, the ICY1 gene, the INM1 gene, the SAP30 gene, the YNL200c gene, the STF2 gene, the SYC1 gene, the YLR326w gene, the YAR028w gene, the YNL024c gene, the YNR034w-a gene, the GPG1 gene, the PDE1 gene, the ADI1 gene, the YNL217w gene, the NRG1 gene, the YPL071c gene, the TMA10 gene, the GRX8 gene, the PFK27 gene, the FKH2 gene, the EEB1 gene, the YLR346c gene, the QCR10 gene, the ATG8 gene, the YER188w gene.

The gene for an acetic acid-responsive transcription factor may be endogenous or exogenous to a host microorganism. For example, with respect to Haa1, a gene derived from *Saccharomyces cerevisiae* may be used, and the base sequence of this gene is as shown in SEQ ID NO: 1 (the encoded amino acid sequence of which is shown in SEQ ID NO: 2). Moreover, a known gene for an acetic acid-responsive transcription factor can be used as appropriate; the present invention is not limited to the above exemplified gene. The gene can be of any origin. That is to say, in addition to the aforementioned gene, genes derived from organisms including animals, plants, fungi (molds etc.), bacteria, and the like may also be used. A person skilled in the art would access the home pages of various genetic databases (e.g., NCBI etc.) to appropriately obtain information regarding such genes (for example, the NCBI gene identification number with respect to Haa1 is Gene ID: 856117).

The gene for an acetic acid-responsive transcription factor to be used in the present invention may be a gene encoding a protein that has a certain relation with sequence information disclosed in a database or the like or the sequences of the various genes specifically described herein, as long as the protein has the activity of acetic acid-responsive transcription. In such an embodiment, a gene encoding a protein that is composed of an amino acid sequence, of the disclosed amino acid sequence, in which one or several amino acids are deleted, substituted, or added and that has an enzymatic activity which is to be expressed or whose expression is to be enhanced in the present invention may be used. Any one type, or a combination of two or more types of mutation, that is, deletion, substitution, and addition of the amino acids, may be made to the disclosed amino acid sequence. Also, the total number of such mutations may be, for example, but not particularly limited to, between about 1 and 10, inclusive, or between 1 and 5, inclusive. With respect to examples of amino acid substitution, any substitution may be used as long as the relevant enzymatic activity is provided, but for example, conservative substitution may be used, specifically including substitution within the following groups (i.e., between the amino acids in parentheses): (glycine, alanine) (valine, isoleucine, leucine) (aspartic acid, glutamic acid) (asparagine, glutamine) (serine, threonine) (lysine, arginine) (phenylalanine, tyrosine).

In another embodiment, the gene to be used in the present invention may be a gene encoding a protein that has an amino acid sequence having, for example, 70% or greater sequence identity with respect to a disclosed amino acid sequence and that has an enzymatic activity which is to be expressed or whose expression is to be enhanced in the present invention. The sequence identity may also be 74% or greater, 78% or greater, 80% or greater, 85% or greater, 90% or greater, 95% or greater, or 98% or greater.

The sequence identity or similarity as used herein refers to, as is known in the art, the relation between two or more proteins or two or more polynucleotides that is determined by comparing the sequences. The "identity" of sequences means the degree of sequence invariance between protein or polynucleotide sequences as determined by an alignment between the protein or polynucleotide sequences or in some cases by an alignment between a series of partial sequences. Also, the "similarity" means the degree of correlation between protein or polynucleotide sequences as determined by an alignment between the protein or polynucleotide sequences or in some cases by an alignment between a series of partial sequences. More specifically, the similarity is determined based on the sequence identity and conservativeness (substitution that maintains a particular amino acid in a sequence or physicochemical properties of a sequence). It should be noted that the similarity is called "Similarity" in sequence homology search results of BLAST, which will be described later. It is preferable that the method for determining the identity and similarity is a method that is designed so that the alignment between sequences to be compared becomes the longest. Methods for determining the identity and similarity are offered as programs available to the public. For example, the BLAST (Basic Local Alignment Search Tool) program by Altschul et at (e.g., Altschul et al., J. Mol. Biol., 1990, 215:403-410; Altschul et al., Nucleic Acids Res., 1997, 25:3389-3402) can be used for determination. Although there is no particular limitation on the conditions in the case where software such as BLAST is used, it is preferable to use default values.

In still another embodiment, a gene may be used that hybridizes under a stringent condition with DNA composed of a base sequence that is complementary to DNA composed of the disclosed base sequence. The stringent condition refers to any condition under which, for example, a so-called specific hybrid is formed while no nonspecific hybrid is formed. For example, conditions may be used under which a complementary strand of a nucleic acid whose base sequence has high identity, that is, DNA composed of a base sequence having, for example, 65% or greater, 70% or greater, 75% or greater, 78% or greater, 80% or greater, 85% or greater, 90% or greater, 95% or greater, or 98% or greater identity with respect to the disclosed base sequence hybridizes, while a complementary strand of a nucleic acid having homology lower than that does not hybridize. More specifically, such conditions include a sodium salt concentration of, for example, 15 to 750 mM, 50 to 750 mM, or 300 to 750 mM, a temperature of, for example, 25 to 70° C., 50 to 70° C., or 55 to 65° C., and a formamide concentration of, for example, 0 to 50%, 20 to 50%, or 35 to 45%. Furthermore, under the stringent conditions, washing conditions for a filter after the hybridization include a sodium salt concentration of, for example, 15 to 600 mM, 50 to 600 mM, or 300 to 600 mM and a temperature of, for example, 50 to 70° C., 55 to 70° C., or 60 to 65° C. In yet another embodiment, a gene containing DNA that has a base sequence having, for example, 65% or greater, 70% or greater, 75% or greater, 78% or greater, 80% or greater, 85% or greater, 90% or greater, 95% or greater, or 98% or greater identity with respect to a disclosed base sequence and that encodes a protein having an enzymatic activity which is to be expressed or whose expression is to be enhanced in the present invention may be used.

Such a gene can be obtained as a nucleic acid fragment by, for example, performing PCR amplification using primers designed based on the disclosed or a known base sequence, with a nucleic acid derived from DNA extracted from various organisms, various cDNA libraries or genomic DNA libraries, or the like as a template. The gene can also be obtained as a nucleic acid fragment by performing hybridization using as a template, a nucleic acid derived from the aforementioned libraries or the like and as a probe, a DNA fragment constituting a part of a gene encoding an enzyme expressed or to be expressed according to the present invention. Alternatively, the gene may be synthesized as a nucleic acid fragment by any known nucleic acid sequence synthesizing procedure, such as chemical synthesis, in the art.

Moreover, the gene can be obtained by, for example, modifying DNA encoding the disclosed or a known amino acid sequence by commonly used mutagenesis, site-specific mutagenesis, molecular evolution using error-prone PCR, or the like. Examples of such approaches include known approaches, such as the Kunkel method or the gapped duplex method, or equivalent methods thereof, and for example, a mutation is introduced using a mutation introducing kit (e.g., Mutant-K (manufactured by Takara Bio Inc.) or Mutant-G (manufactured by Takara Bio Inc.)) or the like that uses site-directed mutagenesis or using a LA PCR in vitro Mutagenesis Kit from Takara Bio Inc.

The gene may be codon optimized so that its expression in the host microorganism is optimized. The codon optimization can be conducted using any means and apparatuses usually used by those skilled in the art.

In the host microorganism, there is no limitation on the form in which expression of the gene encoding an acetic acid-responsive transcription factor is enhanced. It is sufficient if an increase in production amount or activity of the protein encoded by such a gene is seen as compared with that before modification for enhancing expression of that gene. An example of embodiments in which expression of the gene is enhanced is an embodiment in which any endogenous gene is linked so as to be under the control of a stronger promoter which may be either a constitutive promoter or an inducible promoter. Moreover, an embodiment in which any of endogenous and/or exogenous genes is additionally introduced may be given as an example. The additionally introduced gene is retained such that a strong promoter such as, preferably, a constitutive promoter can allow the gene to operate. Herein, the enhancement of expression may also be referred to as "overexpression".

To introduce the gene for an acetic acid-responsive transcription factor into a xylose-utilizing yeast, the gene for the acetic acid-responsive transcription factor is preferably inserted into a plasmid. The plasmid preferably contains a selectable marker and a replication gene for *Escherichia coli* to facilitate the preparation of a plasmid and detection of a transformant. Examples of selectable markers include, but not particularly limited to, drug resistant genes and auxotrophic genes. Examples of drug resistant genes include, but not particularly limited to, ampicillin resistant gene ($Amp^r$) and kanamycin resistant gene ($Kan^r$). Examples of auxotrophic genes include, but not particularly limited to, genes for N-(5'-phosphoribosyl)anthranilate isomerase (TRP1), tryptophan synthase (TRP5), β-isopropylmalate dehydrogenase (LEU2), imidazoleglycerol phosphate dehydrogenase (HIS3), histidinol dehydrogenase (HIS4), dihydroorotic acid dehydrogenase (URA1), and orotidine-5-phosphate decarboxylase (URA3). A replication gene for yeast is not necessarily needed. The plasmid preferably contains a suitable promoter and terminator to express the gene for an acetic acid-responsive transcription factor in a yeast, including, but not particularly limited to, promoters and terminators of genes for triose phosphate dehydrogenase (TDH3), phosphoglycerate kinase (PGK), glyceraldehyde 3'-phosphate dehydrogenase (GAPDH), and glyceraldehyde 3'-phosphate dehydrogenase (GAP). The plasmid contains, if necessary, a gene necessary for homologous recombination, including, but not particularly limited to, Trp1, LEU2, HIS3, and URA3. The plasmid contains a secretion signal sequence as necessary. The above-described plasmid may be prepared as described in Example 1 below, but the present invention is not particularly limited thereto. For example, pIU-GluRAG-SBA and pIH-GluRAG-SBA as described in R. Yamada et al., Enzyme Microb. Technol., 2009, vol. 44, pp. 344-349 may also be used. The gene for an acetic acid-responsive transcription factor is inserted between the promoter and the terminator of such plasmids.

When introducing a plasmid having the gene for an acetic acid-responsive transcription factor into a xylose-utilizing yeast, it is preferable to cut one location of the plasmid so as to create a linearized form so that such a gene can be integrated into the chromosome by homologous recombination.

A transformed yeast that overexpresses the gene for an acetic acid-responsive transcription factor can be produced in this manner. Overexpression of the gene for an acetic acid-responsive transcription factor can be verified with the procedure commonly known to those skilled in the art such as RT-PCR.

In one embodiment, the xylose-utilizing yeast overexpressing the gene for an acetic acid-responsive transcription factor as mentioned above (transformed yeast overexpressing a gene for an acetic acid-responsive transcription factor) is deficient in a PHO13 gene, that is, can be a xylose-utilizing yeast overexpressing the gene for an acetic acid-responsive transcription factor and being deficient in a PHO13 gene, and in one embodiment, may be a xylose-utilizing yeast overexpressing Haa1 and being deficient in a PHO13 gene.

The PHO13 gene is predicted to be for an alkaline phosphatase, but its function and specific substrate within a cell are unclear. A yeast into which the genes for xylose reductase, xylitol dehydrogenase, and xylulokinase, which are xylose-utilizing enzymes, have been introduced and which has been made deficient in the PHO13 gene may have an improved xylose-utilizing ability and maintain a fermentation ability in the presence of acetic acid, formic acid, or furfural (K. Fujitomi et al., Bioresour. Technol., 2012, vol. 111, pp. 161-166). The NCBI gene identification number with respect to the PHO13 gene is Gene ID: 851362. The base sequence of the PHO13 gene derived from *Saccharomyces cerevisiae* and the encoded amino acid sequence thereof are shown in SEQ ID NOs: 3 and 4, respectively.

A yeast deficient in a PHO13 gene may be prepared by suppressing expression of that gene in the yeast. Embodiments in which the gene expression is suppressed may be achieved by suppression of the amount of a normal protein produced and production or promotion of a dysfunctional mutant protein. Examples of gene manipulation to be performed for this purpose include transgenic, gene knock-out, knock-in, and other approaches. For example, a xylose-utilizing yeast deficient in a PHO13 gene may be prepared according to the procedure described in the aforementioned document by K. Fujitomi et al.

Method for Producing Ethanol from Biomass

According to the method for producing ethanol from biomass of the present invention, a transformed yeast that overexpresses a gene for an acetic acid-responsive transcription factor is combined with a saccharified biomass, and the transformed yeast is cultured. Although a fermentation inhibitor, such as acetic acid, occurring due to overdegradation of biomass may be present in the saccharified biomass, the transformed yeast of the present invention is tolerant to such a fermentation inhibitor, and thus proceeds with ethanol fermentation without inhibition to produce ethanol in a culture solution.

The method for producing ethanol from a biomass according to the present invention includes the step of culturing a xylose-utilizing yeast transformed so as to overexpress a gene for an acetic acid-responsive transcription factor in combination with a saccharified biomass (herein, this culturing step may also be referred to as the fermenting step).

The Biomass refers to industrial resources originating from constituents of extant organisms and not being exhaustible resources, or in other words, renewable and biological organic resources excluding fossil resources. Examples of biomass include, but not particularly limited to, resource crops or wastes thereof. Examples of resource crops include, but not particularly limited to, corn and sugar cane, and examples of wastes of the resource crops include wastes generated during processing of the resource crops. Lignocellulose-based biomass is preferably used to avoid the competition with food, including, but not particularly limited to, parts (e.g., chaff, roots, stems, and leaves) of gramineous plants such as rice, barley and wheat, *Miscanthus sinensis*, and reed, excluding those parts that constitute food, as well as wastes generated from products made from such parts.

The saccharification of biomass refers to degradation of polysaccharide in biomass to oligosaccharide or monosaccharide, including further overdegradation of the monosaccharide. Examples of the process for saccharification to be employed in the present invention include, but not particularly limited to, enzymatic treatment, treatment with diluted sulfuric acid, and hydrothermal treatment. In terms of cost, treatment with diluted sulfuric acid and hydrothermal treatment are preferable. In treatment with diluted sulfuric acid, for example, biomass is treated with 1 to 5% diluted sulfuric acid at 180 to 200° C. for about 5 minutes to 1 hour. In hydrothermal treatment, for example, biomass is treated with water at 130 to 300° C. and about 10 MPa.

The saccharified biomass refers to a composition obtained by the saccharification of biomass. The saccharified biomass contains monosaccharide generated from polysaccharide by degradation as the main component, and also contains undegraded oligosaccharide or polysaccharide as well as a by-product generated due to overdegradation. Examples of the by-product generated due to overdegradation include, but not particularly limited to, weak acids such as acetic acid and formic acid, aldehydes such as furfural and hydroxymethylfurfural (HMF), and phenols such as vanillin.

The above-described transformed yeast can be cultured under aerobic conditions prior to fermentation to increase the amount of yeast cells. Culturing the transformed yeast can be suitably carried out with the procedure commonly known to those skilled in the art. The pH of the medium is, for example, 4 to 6, and preferably 5. The dissolved oxygen concentration in the medium during aerobic culture is, for example, 0.5 to 6 ppm, preferably 1 to 4 ppm, and more preferably 2 ppm. The temperature for culture is, for example, 20 to 45° C., preferably 25 to 35° C., and more preferably 30° C. Preferably, the transformed yeast is cultured until the amount of yeast cells becomes, for example, 10 g (wet weight)/L or greater, preferably 25 g (wet weight)/L, and more preferably 37.5 g (wet weight)/L or greater, and the culture period is, for example, about 20 to 50 hours.

In the fermenting step, culture conditions generally applied to yeasts can be selected and used as appropriate. Typically, static culture, shake culture, aerated and agitated culture, or the like can be used for the culture for fermentation. The aerated conditions can be selected as appropriate from anaerobic conditions, microaerophilic conditions, aerobic conditions, and the like. The temperature for culture may be, for example, 25° C. to 40° C., preferably 28° C. to 35° C., and more preferably 30° C. The culture period may be set at any desired time period as necessary and, for example, can be set at a culture period within a range of 6 hours to 24 hours, 12 hours to 36 hours, 24 hours to 50 hours, or the like. The pH can be adjusted using an inorganic or organic acid, an alkaline solution, or the like. The fermentation medium can further contain, in addition to the saccharified biomass, a medium component that may be added to culture the yeast.

After the end of ethanol fermentation, a step of collecting an ethanol-containing fraction from the culture solution (fermentation liquid) and furthermore a step of refining or concentrating this fraction can also be conducted. These steps and methods required for these steps may be selected as appropriate by those skilled in the art.

The yeast according to the present invention is tolerant to various fermentation inhibitors, including acetic acid, formic acid, and aldehydes such as furfural, which are contained in a saccharified biomass subjected to pretreatment such as hydrothermal treatment. Ethanol can be efficiently produced by ethanol fermentation from xylose using the yeast according to the present invention with a saccharified biomass which contains various fermentation inhibitors.

EXAMPLES

The present invention will be described in detail below by way of examples, but the present invention is not limited to the examples below.

Example 1

Ethanol Fermentation Test from Xylose in the Presence of Acetic Acid Using Xylose-Utilizing Yeast Overexpressing Haa1

Preparation of Plasmid for Overexpression of Haa1

A plasmid for overexpressing the Haa1 gene in a yeast was constructed.

First, pRS405+2 µm (prepared in the same manner as described in J. Ishii et al., J. Biochem., 2009, vol. 145, pp. 701-708) was cut with restriction enzymes SacI and SalI. Fragments of a TDH3 promoter and a TDH terminator obtained by similarly cutting the triose phosphate dehydrogenase (TDH3) gene derived from the yeast *Saccharomyces cerevisiae* gene with restriction enzymes SacI and SacII were linked together, and the TDH3 promoter and the TDH3 terminator were inserted into a multiple cloning site of pRS405+2 µm to obtain pRS405pTDH3. Then, the Haa1 gene (SEQ ID NO: 1: the predicted amino acid sequence of which is shown in SEQ ID NO: 2) derived from the yeast *Saccharomyces cerevisiae* was inserted between the TDH3 promoter and the TDH3 terminator of pRS405pTDH3 to prepare a plasmid pRS425pTDH3-Haa1.

The Haa1 gene to be inserted was prepared by obtaining a DNA fragment by a commonly used PCR procedure with primers Haa1-F (SEQ ID NO: 5) and Haa1-R (SEQ ID NO: 6), using genomic DNA extracted from MT8-1 strain (MATa) of the yeast *Saccharomyces cerevisiae* by a commonly used procedure as a template, and treating this fragment with restriction enzymes NotI and SalI. The obtained plasmid pRS425pTDH3-Haa1 has the $Amp^r$ gene which imparts ampicillin resistance to the transformant.

Preparation of Xylose-Utilizing Yeast Overexpressing Haa1

Into BY4741 strain (Invitrogen) of the yeast *Saccharomyces cerevisiae*, the plasmid pIUX1X2XK for imparting a xylose-utilizing ability (prepared as described in S. Katahira et al., Appl. Microbiol. Biotechnol., 2006, vol. 72, pp. 1136-1143 as the plasmid for coexpressing xylose reductase (XR) and xylitol dehydrogenase (XDH) derived from the yeast *Pichia stipitis* and xylulokinase (XK) derived from the yeast *Saccharomyces cerevisiae*) was introduced by lithium acetate treatment, to produce a xylose-utilizing transformed yeast BY4741XU strain.

The plasmid pRS425pTDH3-Haa1 or the plasmid pRS425pTDH3 (used as a control) were introduced into the above xylose-utilizing transformed yeast BY4741XU strain by lithium acetate treatment to prepare strains BY4741XU/pIUX1X2XK/pRS425pTDH3-Haa1 (pRS425pTDH3/Haa1 strain), and BY4741XU/pIUX1X2XK/pRS425pTDH3 (pRS425pTDH3 (control) strain). These strains were each cultured in an SD-HM solid medium (Yeast Nitrogen Base without Amino Acids (manufactured by Difco) 6.7 g/L, glucose 20 g/L, histidine 0.02 g/L, and methionine 0.02 g/L).

Haa1 Gene Expression Test in Haa1-Overexpressing Strain

The expression of the Haa1 gene in the pRS425pTDH3/Haa1 strain (Haa1-overexpressing strain) was investigated in the following manner. A fermentation liquid (xylose 50 g/L, yeast extract 10 g/L, Bacto Peptone 20 g/L, calcium casaminate 1.0 g/L, and yeast 40 g/L: total amount 50 mL) was prepared, culture was then performed at 30° C. for 1 hour, and yeast cells were sampled. The pRS425pTDH3 (control) strain was used as a control strain. RNA was extracted from the obtained samples, and after cDNA synthesis, relative values of Haa1 expression in the Haa1-overexpressing strain and the control strain were calculated by quantitative PCR. The calculation was performed by the comparative Ct method using the actin gene as a control gene. Table 1 below shows the results.

TABLE 1

| Strain | actin (ACT1) $C_T$ | Haa1 $C_T$ | $\Delta C_T$ ACT1 - Haa1 | $\Delta\Delta C_T$ $\Delta C_T -$ $\Delta C_T$ACT1 | Relative level of expression of Haa1 * |
|---|---|---|---|---|---|
| Control strain | 28.39 | 30.35 | 1.96 | 0 | 1 |
| Haa1-overexpressing strain | 29.38 | 30.94 | 1.56 | −0.4 | 1.32 |

* Calculated by substitution for $2^{-\Delta\Delta C_T}$.

As is clear from Table 1, it was verified that the expression of the Haa1 gene in the Haa1-overexpressing strain was increased as compared with that in the control strain.

Fermentation Test in the Presence of Acetic Acid for Haa1-Overexpressing Strain

Ethanol fermentation from xylose in the presence of acetic acid was performed using the Haa1-overexpressing strain or the control strain. The Haa1-overexpressing strain or the control strain was precultured in an SD medium for 1 day, then cultured in the SD medium for 2 days, and subjected to fermentation thereafter. To a YP medium with xylose at an initial concentration of 50 g/L and yeast cells at 40 g/L (wet weight), no acetic acid was added (0 mM) or acetic acid was added at a concentration of 30 mM or 60 mM, and then fermentation culture of the yeast was started. Table 2 shows the schema of the fermentation test.

TABLE 2

| Preculture | SD medium-1 day |
|---|---|
| Main culture ↓ | SD medium-2 days |
| Fermentation | 30° C., 500 rpm |

| Composition of fermentation liquid | |
|---|---|
| Component | Concentration |
| Xylose | 50 g/L |
| Yeast extract | 10 g/L |
| Bacto Peptone | 20 g/L |
| Calcium pantothenate | 1.6 g/L |
| Yeast | 40 g/L |
| Acetic acid | 0, 30, 60 mM |
| Total | 50 mL |

The amounts of xylose and produced ethanol in the medium were determined over time by HPLC (High performance liquid chromatography system; manufactured by Shimadzu Corporation) using Shim-pack SPR-Pb (manufactured by Shimadzu Corporation) as a separation column, ultrapure water (water purified by Milli-Q manufactured by Nihon Millipore K.K.) as a mobile phase, and a refractive index detector as a detector under conditions of a flow rate of 0.6 mL/min and a temperature of 80° C.

The results are shown in FIG. 1. The results of the control strain for 0 mM, 30 mM, and 60 mM acetic acid, are shown in (A) to (C) of FIG. 1, respectively, and the results of the Haa1-overexpressing strain for 0 mM, 30 mM, and 60 mM acetic acid are shown in (D) to (F) of FIG. 1, respectively. In FIG. 1, hollow diamond shapes indicate the xylose concentration, and hollow rectangles indicate the ethanol concentration.

As is clear from FIG. 1, regarding the control strain, the xylose consumption rate was decreased with increase in acetic acid concentration, and both the production rate and amount of ethanol were decreased accordingly. It is thus found that the presence of acetic acid considerably inhibits ethanol fermentation from xylose.

In contrast, regarding the Haa1-overexpressing strain, when compared with the control strain, both the final amount of xylose consumed and the final amount of ethanol produced significantly increased either in the absence of acetic acid or in the presence of 30 mM or 60 mM acetic acid. Also, the ethanol yield exceeded 80% of the theoretical yield at 30 mM acetic acid, and exceeded 50% even at 60 mM acetic acid. It should be noted that for the control strain, the ethanol yield was 33% at 60 mM acetic acid.

Example 2

Ethanol Fermentation Test from Xylose in the Presence of Formic Acid Using Xylose-Utilizing Yeast Overexpressing Haa1

Ethanol fermentation from xylose in the presence of formic acid was performed using the Haa1-overexpressing strain or the control strain. Ethanol fermentation in this example was performed in the same manner as in Example 1 except that, to a YP medium with xylose at an initial concentration of 50 g/L and yeast cells at 40 g/L (wet weight), no formic acid was added (0 mM) or formic acid was added at a concentration of 20 mM, and each resulting medium was used for fermentation culture. Table 3 shows the schema of the fermentation test.

TABLE 3

| Preculture | SD medium-1 day |
|---|---|
| Main culture ↓ | SD medium-2 days |
| Fermentation | 30° C., 500 rpm |

| Composition of fermentation liquid | |
|---|---|
| Component | Concentration |
| Xylose | 50 g/L |
| Yeast extract | 10 g/L |
| Bacto Peptone | 20 g/L |
| Calcium casaminate | 1.0 g/L |
| Yeast | 40 g/L |
| Formic acid | 0 or 20 mM |
| Total | 50 mL |

The amounts of xylose and produced ethanol in the medium were determined over time in the same manner as in Example 1. The results are shown in FIG. 2 (FIG. 2 (A): 0 mM formic acid, (B): 20 mM formic acid).

Figure 2:
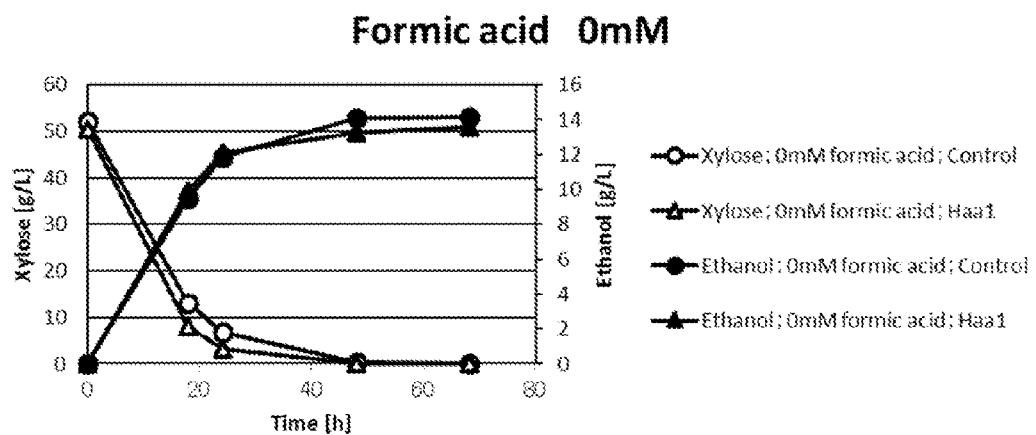
FIG. 2 represents graphs showing changes over time in the concentrations of the substrate (xylose) and the product (ethanol) in the fermentation liquid with respect to strains pRS425pTDH3/Haa1 (Haa1-overexpressing strain) and pRS425pTDH3 (control strain) where ethanol fermentation from xylose is performed in the absence of formic acid (0 mM: A) and in the presence of 20 mM formic acid (B).
Figure 2:
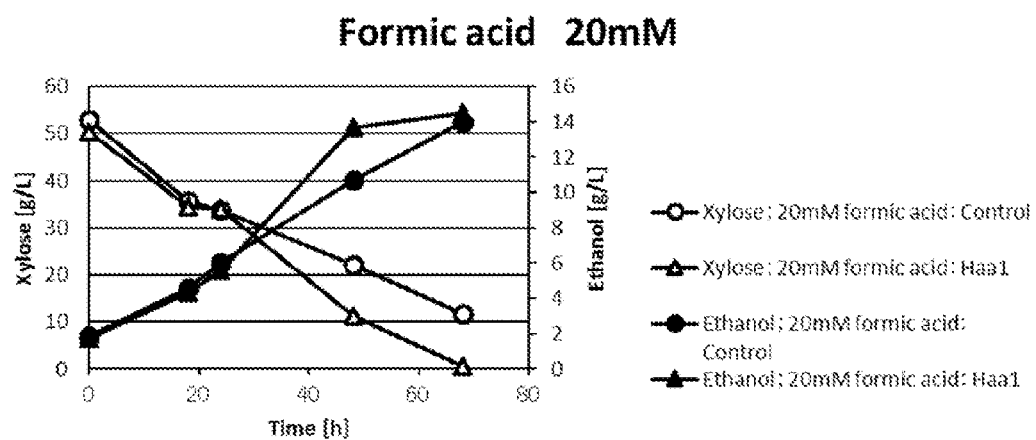

As is clear from FIG. 2, regarding the control strain, the addition of formic acid caused a decrease in the consumption rate of xylose (in FIG. 2, indicated by hollow circles), and both the production rate and amount of ethanol (in FIG. 2, indicated by solid circles) were decreased accordingly. It is thus found that the presence of formic acid considerably inhibits ethanol fermentation from xylose.

In contrast, regarding the Haa1-overexpressing strain, when compared with the control strain, in the presence of 20 mM formic acid, both the xylose consumption amount and ethanol production rate were increased (in FIG. 2, the amount of xylose is indicated by hollow triangles, and the amount of ethanol is indicated by solid triangles). The ethanol yield also exceeded 80% of the theoretical yield.

Example 3

Growth Test in the Presence of Furfural Using Xylose-Utilizing Yeast Overexpressing Haa1

A growth culture test in the presence of furfural was performed using the Haa1-overexpressing strain and the control strain. A culture solution having a composition shown in Table 4 below was prepared, and then culture of the yeasts was started. The culture was performed at 30° C. with shaking at 70 rpm. The amount of cells grown was determined over time by absorbance measurement ($OD_{600}$) at a wavelength of 600 nm.

TABLE 4

| Composition of culture solution | |
|---|---|
| Component | Concentration |
| Glucose | 20 g/L |
| Yeast extract | 10 g/L |
| Bacto Peptone | 20 g/L |
| Yeast | $OD_{600}$ = 0.05 |
| Furfural | 0 or 5 mM |
| Total | 5 mL |

Figure 3:
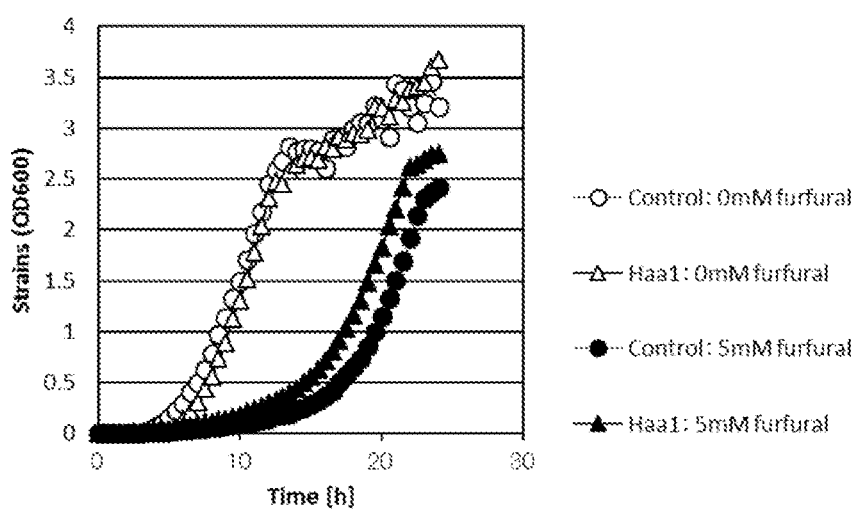
FIG. 3 is a graph showing changes over time in the amount of cells grown during culture in the absence of furfural (0 mM) and in the presence of 5 mM furfural with respect to strains pRS425pTDH3/Haa1 (Haa1-overexpressing strain) and pRS425pTDH3 (control strain).

The results are shown in FIG. 3. As is clear from FIG. 3, regarding the control strain, the growth in the presence of furfural (in FIG. 3, indicated by solid circles) was retarded as compared with that in the absence of furfural (in FIG. 3, indicated by hollow circles). Regarding the Haa1-overexpressing strain, the growth in the presence of furfural (in FIG. 3, indicated by solid triangles) was retarded as compared with that in the absence of furfural (in FIG. 3, indicated by hollow triangles), of which the growth retardation was suppressed more than that of the control strain.

With regard to the Haa1-overexpressing strain and the control strain, the time until the amount of cells grown ($OD_{600}$) reached $OD_{600}$=0.5 was also investigated. Table 5 below shows the results.

TABLE 5

| | Concentration [mM] | | |
|---|---|---|---|
| | 0 | 5 | Growth retardation time [hour] |
| Control | 7 | 17 | 10 |
| Haa1 | 8 | 14.5 | 6.5 |

As is also clear from Table 5, in the presence of furfural, the growth retardation of the Haa1-overexpressing strain was suppressed more than that of the control strain.

Example 4

Growth Test in the Presence of Acetic Acid Using Haa1 Overexpressing, PHO13-Deficient, Xylose-Utilizing Yeast A Haa1-overexpressing, PHO13-deficient, xylose-utilizing yeast (hereinafter referred to as "Haa1-overexpressing, PHO13-deficient strain") was obtained by making the Haa1-overexpressing strain described in Example 1 to be PHO13-deficient according to the procedure described in K. Fujitomi et al., Bioresour. Technol., 2012, vol. 111, pp. 161-166. On the other hand, a PHO13-deficient, xylose-utilizing yeast (hereinafter referred to as "PHO13-deficient control strain") was also obtained by making the control strain (pRS425pTDH3 strain) described in Example 1 to be PHO13-deficient in the same manner.

A growth culture test in the presence of acetic acid was performed using the Haa1-overexpressing strain and the control strain as well as the Haa1-overexpressing, PHO13-deficient strain and the PHO13-deficient control strain. A culture solution having a composition shown in Table 6 below was prepared, and then culture of the yeasts was started. The culture was performed at 30° C. with shaking at 120 rpm. After 72 hours, the amount of cells grown was determined by absorbance measurement ($OD_{600}$) at a wavelength of 600 nm (the initial concentration of cells was set at $OD_{600}$=0.1).

TABLE 6

| Composition of culture solution | |
|---|---|
| Component | Concentration |
| Xylose | 20 g/L |
| Yeast extract | 10 g/L |
| Bacto Peptone | 20 g/L |
| Yeast | $OD_{600}$ = 0.1 |
| Acetic acid | 0, 5, 10, 40, 60, 80 mM |
| Total | 50 mL |

Figure 4:
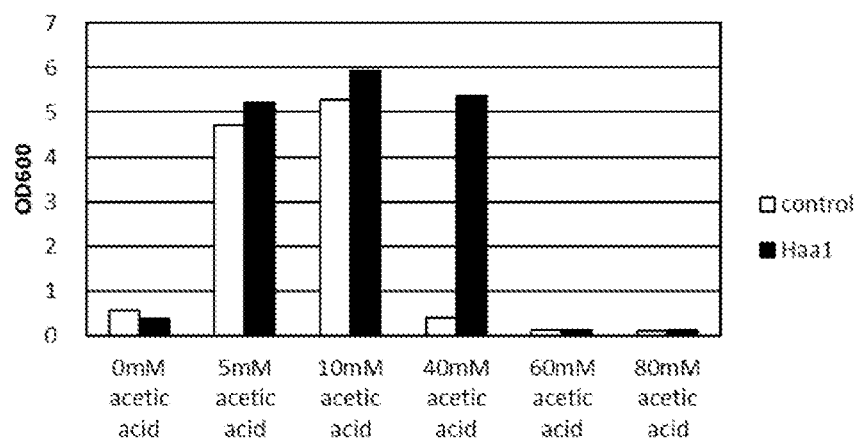
FIG. 4 represents graphs showing the amounts of cells grown after 72 hours of culture in which a Haa1-overexpressing strain and a control strain (A) as well as a Haa1-overexpressing, PHO13-deficient strain and a PHO13-deficient control strain (B) are cultured in the absence of acetic acid (0 mM) and in the presence of acetic acid at various concentrations.
Figure 4:
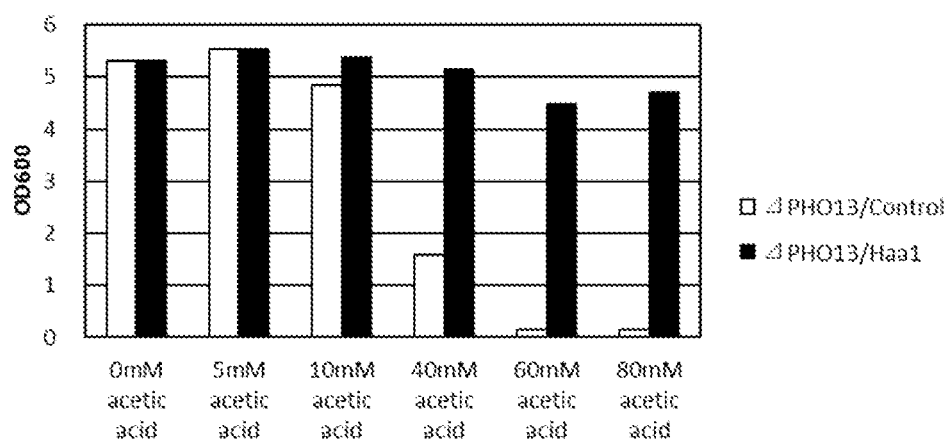

The results are shown in FIG. 4 ((A) Haa1-overexpressing strain and control strain, and (B) Haa1-overexpressing, PHO13-deficient strain and PHO13-deficient control strain). As is clear from FIG. 4(A), when acetic acid was added at 5 mM, 10 mM, and 40 mM, the Haa1-overexpressing strain (indicated by black bars) has improved growth as compared with the control strain (indicated by white bars). Also, as is clear from FIG. 4(B), when acetic acid was added at any concentration, the Haa1-overexpressing, PHO13-deficient strain (indicated by black bars) has improved growth as compared with the PHO13-deficient control strain (indicated by white bars). It was observed that a yeast transformed so as to overexpress Haa1 and made to be PHO13-deficient has grown even in the presence of acetic acid at higher concentrations (for example, 60 mM and 80 mM).

Example 5

Ethanol Fermentation Test from Xylose in the Presence of Acetic Acid Using Haa1-Overexpressing, PHO13-Deficient, Xylose-Utilizing Yeast Using the Haa1-overexpressing, PHO13-deficient strain and the PHO13-deficient control strain, an ethanol fermentation test from xylose in the presence of acetic acid was performed in the same manner as in Example 1, proviso that the concentrations of acetic acid added were set at 0 mM, 50 mM, and 100 mM, and 1.6 g/L of calcium pantothenate was replaced by 1.0 g/L of calcium pantothenate.

Figure 5:
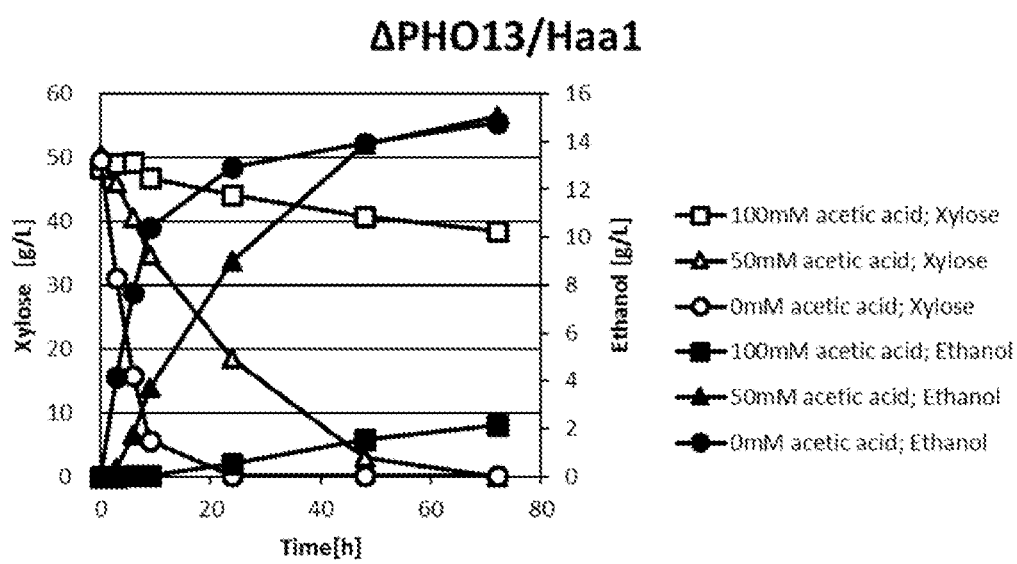
FIG. 5 represents graphs showing changes over time in the concentrations of the substrate (xylose) and the product (ethanol) in the fermentation liquid with respect to a Haa1-overexpressing, PHO13-deficient strain (A) and a PHO13-deficient control strain (B) where ethanol fermentation from xylose is performed in the absence of acetic acid (0 mM) and in the presence of acetic acid (50 mM and 100 mM).
Figure 5:
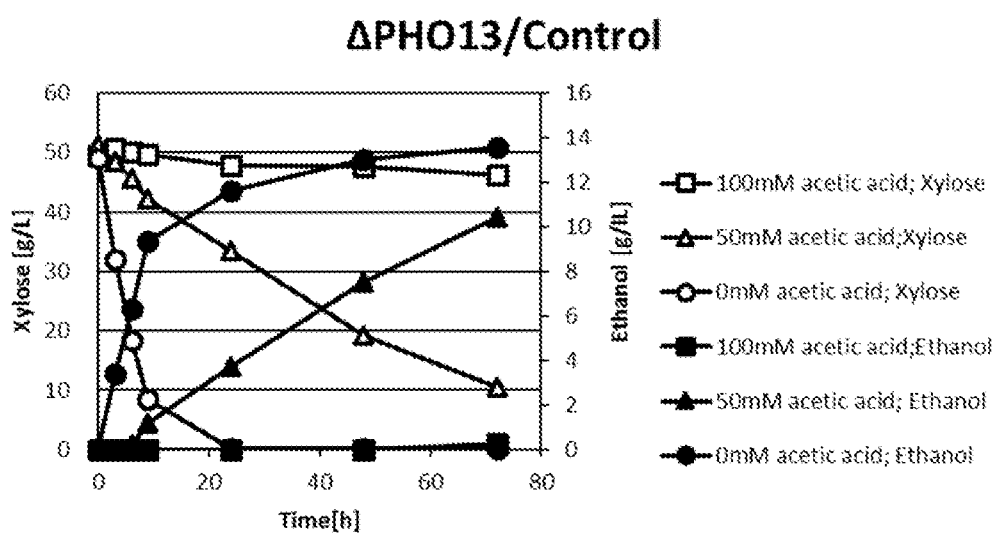

The results are shown in FIG. 5 ((A) Haa1-overexpressing, PHO13-deficient strain and (B) PHO13-deficient control strain). As is clear from (A) and (B) of FIG. 5, the amount of xylose utilized and the amount of ethanol produced of the Haa1-overexpressing, PHO13-deficient strain exceeded those of the PHO13-deficient control strain at either of the acetic acid concentrations 50 mM and 100 mM. Thus, it was observed that a yeast transformed so as to overexpress Haa1 and made to be PHO13-deficient is tolerant even in the presence of acetic acid at a higher concentration (for example, 100 mM) and is able to produce ethanol.

Example 6

Ethanol Fermentation Test in Actual Biomass Using Haa1-Overexpressing, PHO13-Deficient, Xylose-Utilizing Yeast An ethanol fermentation test from xylose in actual biomass was performed using the Haa1-overexpressing, PHO13-deficient strain and the PHO13-deficient control strain A culture solution having a composition shown in Table 7 below was prepared, and then culture of the yeasts was started. The culture was performed at 30° C. with shaking at 120 rpm. The actual biomass (C5 saccharified solution) was prepared by adding, to a solution of degraded rice straw pre-treated by hydrothermal treatment, a saccharifying enzyme (Pectinase G Amano: manufactured by Amano Enzyme Inc.) at a concentration of 1 (w/w) %, and performing saccharification for 2 days under the conditions of 50° C. and 150 rpm. The amount of ethanol produced was determined over time in the same manner as in Example 1.

TABLE 7

| Composition of culture solution | |
|---|---|
| Component | Concentration |
| C5 saccharified solution | 60% (v/v) |
| Yeast extract | 10 g/L |
| Bacto Peptone | 20 g/L |
| Yeast | 40 g/L |

Figure 6:
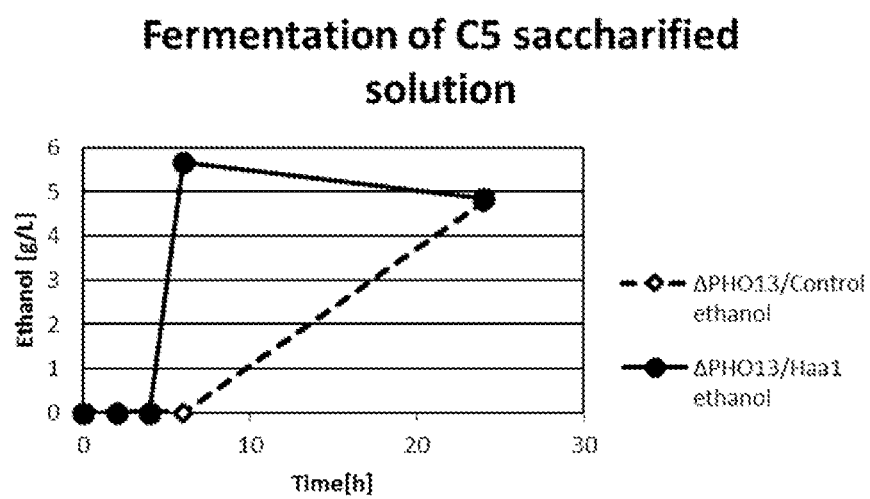
FIG. 6 is a graph showing changes over time in the concentration of ethanol in the fermentation liquid with respect to a Haa1-overexpressing, PHO13-deficient strain (A) and a PHO13-deficient control strain (B) where ethanol fermentation from an actual biomass is performed.

The results are shown in FIG. 6. In FIG. 6, the results after 2 hours, 4 hours, 6 hours, and 24 hours from the start of fermentation are shown. As is clear from FIG. 6, regarding the Haa1-overexpressing, PHO13-deficient strain (solid circles), the amount of ethanol produced sharply increased after 6 hours had elapsed from the start of fermentation. Regarding the PHO13-deficient control strain, no ethanol production was observed in the same time period. It was observed that a yeast transformed so as to overexpress Haa1 and made to be PHO13-deficient exhibits an increase in the rate of ethanol production using an actual biomass.

INDUSTRIAL APPLICABILITY

According to the method of the present invention, ethanol can be efficiently produced by ethanol fermentation from xylose using a saccharified biomass, which contains various fermentation inhibitors. Accordingly, it is possible to produce bioethanol using lignocellulose-based biomass, such as rice straw, straw, and wood scrap, as a raw material to avoid the competition with food, leading to provision of alternatives to fossil fuels, as well as prevention of global warming and solution of food issues.

The invention claimed is:

1. A method for producing ethanol from biomass, comprising the step of:
    culturing a xylose-utilizing yeast transformed so as to overexpress a gene for an acetic acid-responsive transcription factor in combination with a saccharified biomass, wherein the acetic acid-responsive transcription factor is Haa1.

2. The method of claim 1, wherein the transformed xylose-utilizing yeast is deficient in a PHO13 gene.

3. The method of claim 1, wherein the saccharified biomass contains a fermentation inhibitor.

4. The method of claim 3, wherein the fermentation inhibitor is at least one selected from the group consisting of acetic acid, formic acid, furfural, hydroxymethylfurfural, and vanillin.

5. The method of claim 1, wherein the xylose-utilizing yeast is of *Saccharomyces*.

6. The method of claim 5, wherein the *Saccharomyces* is *Saccharomyces cerevisiae*.

* * * * *

SEQUENCE LISTING

```
<160> NUMBER OF SEQ ID NOS: 6

<210> SEQ ID NO 1
<211> LENGTH: 2085
<212> TYPE: DNA
<213> ORGANISM: Saccharomyces cerevisiae
<220> FEATURE:
<221> NAME/KEY: CDS
<222> LOCATION: (1)..(2085)
<223> OTHER INFORMATION: Haa1

<400> SEQUENCE: 1 atg gtc ttg ata aat ggc ata aag tat gcc tgt gag agg tgc ata aga    48
Met Val Leu Ile Asn Gly Ile Lys Tyr Ala Cys Glu Arg Cys Ile Arg
1               5                   10                  15 ggc cat aga gta aca aca tgc aat cat aca gat caa ccg ctt atg atg    96
Gly His Arg Val Thr Thr Cys Asn His Thr Asp Gln Pro Leu Met Met
                20                  25                  30 atc aaa ccc aaa ggt aga cct tcc act aca tgc gac tat tgt aaa caa   144
Ile Lys Pro Lys Gly Arg Pro Ser Thr Thr Cys Asp Tyr Cys Lys Gln
            35                  40                  45 ctt cga aaa aac aag aat gca aat cct gaa ggt gtt tgc acg tgt ggc   192
Leu Arg Lys Asn Lys Asn Ala Asn Pro Glu Gly Val Cys Thr Cys Gly
        50                  55                  60 cgg cta gag aag aaa aaa ctg gca cag aaa gcc aaa gaa gaa gca aga   240
Arg Leu Glu Lys Lys Lys Leu Ala Gln Lys Ala Lys Glu Glu Ala Arg
65                  70                  75                  80 gct aaa gcc aaa gaa aaa caa aga aaa cag tgt acc tgc ggg act gat   288
Ala Lys Ala Lys Glu Lys Gln Arg Lys Gln Cys Thr Cys Gly Thr Asp
                85                  90                  95 gag gtt tgc aaa tat cat gct caa aag aga cat cta aga aag tcc cct   336
Glu Val Cys Lys Tyr His Ala Gln Lys Arg His Leu Arg Lys Ser Pro
            100                 105                 110 tca agt tct caa aag aaa gga aga tcc att tct cgt tct caa cca atg   384
Ser Ser Ser Gln Lys Lys Gly Arg Ser Ile Ser Arg Ser Gln Pro Met
        115                 120                 125 ttt gaa agg gta ttg tct tct act tca ctt gac agc aat atg tta tcc   432
Phe Glu Arg Val Leu Ser Ser Thr Ser Leu Asp Ser Asn Met Leu Ser
    130                 135                 140 ggc cac gga gca cta tca gat acc tct agc ata ctg acg aca ttt        480
Gly His Gly Ala Leu Ser Asp Thr Ser Ser Ile Leu Thr Ser Thr Phe
145                 150                 155                 160 tta gac agt gag ccg ggt gtt ggt aaa att tca aaa gat tac cat cat   528
Leu Asp Ser Glu Pro Gly Val Gly Lys Ile Ser Lys Asp Tyr His His
                165                 170                 175
```

```
gtc cct tca ttg gcc tcc att tca tcc tta caa tcc tcg caa tcg tta      576
Val Pro Ser Leu Ala Ser Ile Ser Ser Leu Gln Ser Ser Gln Ser Leu
            180                 185                 190 gat caa aat ttc agt ata cca caa agc ccg ccg tta tct tca atg tca      624
Asp Gln Asn Phe Ser Ile Pro Gln Ser Pro Pro Leu Ser Ser Met Ser
        195                 200                 205 ttt aat ttt ctc acg gga aat atc aat gaa acc aac caa aat cac agt      672
Phe Asn Phe Leu Thr Gly Asn Ile Asn Glu Thr Asn Gln Asn His Ser
    210                 215                 220 aat cat cag cat tca aaa tca ggc aat aac tgg caa gat agt tcg gta      720
Asn His Gln His Ser Lys Ser Gly Asn Asn Trp Gln Asp Ser Ser Val
225                 230                 235                 240 agc ttg cca gcg aaa gct gat tca cgt ctt aac atg atg gat aaa aac      768
Ser Leu Pro Ala Lys Ala Asp Ser Arg Leu Asn Met Met Asp Lys Asn
                245                 250                 255 aac tct gtg ggt ctt gac cta tta ggc cat tca aaa cga ata tcg ccg      816
Asn Ser Val Gly Leu Asp Leu Leu Gly His Ser Lys Arg Ile Ser Pro
            260                 265                 270 ata tca aac tct cgt gtg ggc gaa gtt agc gtt ccg cta gaa gaa tat      864
Ile Ser Asn Ser Arg Val Gly Glu Val Ser Val Pro Leu Glu Glu Tyr
        275                 280                 285 att cct tct gac att gat ggg gtt gga aga gtt act gat aaa agc tct      912
Ile Pro Ser Asp Ile Asp Gly Val Gly Arg Val Thr Asp Lys Ser Ser
    290                 295                 300 ttg gtc tac gat tgg cca ttt gat gaa agt att gag aga aat ttc agt      960
Leu Val Tyr Asp Trp Pro Phe Asp Glu Ser Ile Glu Arg Asn Phe Ser
305                 310                 315                 320 aca acc gca acc gct gca act ggt gaa agt aag ttc gac att aac gac     1008
Thr Thr Ala Thr Ala Ala Thr Gly Glu Ser Lys Phe Asp Ile Asn Asp
                325                 330                 335 aac tgt aat aga att aat agc aaa agt tat agt aag act aat agt atg     1056
Asn Cys Asn Arg Ile Asn Ser Lys Ser Tyr Ser Lys Thr Asn Ser Met
            340                 345                 350 aat gga aac ggt atg aac aat agc aat aat aat atc aac agt aat         1104
Asn Gly Asn Gly Met Asn Asn Ser Asn Asn Asn Ile Asn Ser Asn
        355                 360                 365 ggc aac gac aag aac aat aac aac tct tct aga caa gaa cat caa gga     1152
Gly Asn Asp Lys Asn Asn Asn Asn Ser Ser Arg Gln Glu His Gln Gly
    370                 375                 380 aat gga cta ttt gac atg ttt aca gat tca tcg tcg att tca acg ctt     1200
Asn Gly Leu Phe Asp Met Phe Thr Asp Ser Ser Ser Ile Ser Thr Leu
385                 390                 395                 400 tcc cgt gca aac tta tta ttg caa gaa aaa att ggt tcg caa gaa aac     1248
Ser Arg Ala Asn Leu Leu Leu Gln Glu Lys Ile Gly Ser Gln Glu Asn
                405                 410                 415 tct gtc aaa caa gaa aac tat tcg aaa aat cct caa ctt cgt cat caa     1296
Ser Val Lys Gln Glu Asn Tyr Ser Lys Asn Pro Gln Leu Arg His Gln
            420                 425                 430 tta act tcc aga agt aga tca ttt att cat cat ccg gca aac gag tat     1344
Leu Thr Ser Arg Ser Arg Ser Phe Ile His His Pro Ala Asn Glu Tyr
        435                 440                 445 ttg aag aat act ttt gga aat tca cat agt aat gac atc gga aag gga     1392
Leu Lys Asn Thr Phe Gly Asn Ser His Ser Asn Asp Ile Gly Lys Gly
    450                 455                 460 gtt gaa gtg cta tct ttg aca ccg agt ttt atg gat att ccc gaa aaa     1440
Val Glu Val Leu Ser Leu Thr Pro Ser Phe Met Asp Ile Pro Glu Lys
465                 470                 475                 480 gaa aga gaa acg gaa aga tcg cca tca tcc aat tac att act gac aga     1488
Glu Arg Glu Thr Glu Arg Ser Pro Ser Ser Asn Tyr Ile Thr Asp Arg
```

```
                         485                 490                 495
cct ttc act cga aaa cct aga tct tct agc att gac gta aac cat agg      1536
Pro Phe Thr Arg Lys Pro Arg Ser Ser Ser Ile Asp Val Asn His Arg
            500                 505                 510 tat cca cct atg gca cca aca acc gta gcg aca tct ccc ggt gca ttg      1584
Tyr Pro Pro Met Ala Pro Thr Thr Val Ala Thr Ser Pro Gly Ala Leu
            515                 520                 525 aac aat gcc gta gca agc aat ctc gac gat caa ctg agt tta aca tca      1632
Asn Asn Ala Val Ala Ser Asn Leu Asp Asp Gln Leu Ser Leu Thr Ser
        530                 535                 540 cta aac tct cag cca tca tcg ata gca aat atg atg atg gac cct tca      1680
Leu Asn Ser Gln Pro Ser Ser Ile Ala Asn Met Met Met Asp Pro Ser
545                 550                 555                 560 aac cta gct gag caa agt tct att cat tca gtt cct cag tca ata aac      1728
Asn Leu Ala Glu Gln Ser Ser Ile His Ser Val Pro Gln Ser Ile Asn
                565                 570                 575 tct ccg aga atg cct aaa act gga agt cgc caa gac aag aac att cac      1776
Ser Pro Arg Met Pro Lys Thr Gly Ser Arg Gln Asp Lys Asn Ile His
            580                 585                 590 act aag aag gaa gaa aga aat ccg cta aat aac ata cac gat ctg tca      1824
Thr Lys Lys Glu Glu Arg Asn Pro Leu Asn Asn Ile His Asp Leu Ser
        595                 600                 605 caa ttg gaa aat gta cca gac gag atg aac caa atg ttc tcc cca cca      1872
Gln Leu Glu Asn Val Pro Asp Glu Met Asn Gln Met Phe Ser Pro Pro
    610                 615                 620 tta aaa agt atg aat aga ccg gat gcc ata agg gaa aat tca tct agt      1920
Leu Lys Ser Met Asn Arg Pro Asp Ala Ile Arg Glu Asn Ser Ser Ser
625                 630                 635                 640 agt aat ttc ata atc caa gga aat agc atg atc tct acg cct tcc gga      1968
Ser Asn Phe Ile Ile Gln Gly Asn Ser Met Ile Ser Thr Pro Ser Gly
                645                 650                 655 agg aat gac ctt cca gat acc tct cca atg agt agt att caa aca gcg      2016
Arg Asn Asp Leu Pro Asp Thr Ser Pro Met Ser Ser Ile Gln Thr Ala
            660                 665                 670 tca cca cca agt caa tta ctg acc gat caa gga ttt gcg gat ttg gat      2064
Ser Pro Pro Ser Gln Leu Leu Thr Asp Gln Gly Phe Ala Asp Leu Asp
        675                 680                 685 aat ttc atg tct tcg tta tga                                          2085
Asn Phe Met Ser Ser Leu
    690

<210> SEQ ID NO 2
<211> LENGTH: 694
<212> TYPE: PRT
<213> ORGANISM: Saccharomyces cerevisiae

<400> SEQUENCE: 2

Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

Arg Leu Glu Lys Lys Lys Leu Ala Gln Lys Ala Lys Glu Glu Ala Arg
65                  70                  75                  80

Ala Lys Ala Lys Glu Lys Gln Arg Lys Gln Cys Thr Cys Gly Thr Asp
                85                  90                  95
```

-continued

```
Glu Val Cys Lys Tyr His Ala Gln Lys Arg His Leu Arg Lys Ser Pro
            100                 105                 110
Ser Ser Ser Gln Lys Lys Gly Arg Ser Ile Ser Arg Ser Gln Pro Met
        115                 120                 125
Phe Glu Arg Val Leu Ser Ser Thr Ser Leu Asp Ser Asn Met Leu Ser
130                 135                 140
Gly His Gly Ala Leu Ser Asp Thr Ser Ser Ile Leu Thr Ser Thr Phe
145                 150                 155                 160
Leu Asp Ser Glu Pro Gly Val Gly Lys Ile Ser Lys Asp Tyr His His
                165                 170                 175
Val Pro Ser Leu Ala Ser Ile Ser Ser Leu Gln Ser Ser Gln Ser Leu
            180                 185                 190
Asp Gln Asn Phe Ser Ile Pro Gln Ser Pro Leu Ser Ser Met Ser
        195                 200                 205
Phe Asn Phe Leu Thr Gly Asn Ile Asn Glu Thr Asn Gln Asn His Ser
    210                 215                 220
Asn His Gln His Ser Lys Ser Gly Asn Asn Trp Gln Asp Ser Ser Val
225                 230                 235                 240
Ser Leu Pro Ala Lys Ala Asp Ser Arg Leu Asn Met Met Asp Lys Asn
                245                 250                 255
Asn Ser Val Gly Leu Asp Leu Leu Gly His Ser Lys Arg Ile Ser Pro
            260                 265                 270
Ile Ser Asn Ser Arg Val Gly Glu Val Ser Val Pro Leu Glu Glu Tyr
        275                 280                 285
Ile Pro Ser Asp Ile Asp Gly Val Gly Arg Val Thr Asp Lys Ser Ser
        290                 295                 300
Leu Val Tyr Asp Trp Pro Phe Asp Glu Ser Ile Glu Arg Asn Phe Ser
305                 310                 315                 320
Thr Thr Ala Thr Ala Ala Thr Gly Glu Ser Lys Phe Asp Ile Asn Asp
                325                 330                 335
Asn Cys Asn Arg Ile Asn Ser Lys Ser Tyr Ser Lys Thr Asn Ser Met
            340                 345                 350
Asn Gly Asn Gly Met Asn Asn Ser Asn Asn Asn Ile Asn Ser Asn
        355                 360                 365
Gly Asn Asp Lys Asn Asn Asn Asn Ser Ser Arg Gln Glu His Gln Gly
        370                 375                 380
Asn Gly Leu Phe Asp Met Phe Thr Asp Ser Ser Ile Ser Thr Leu
385                 390                 395                 400
Ser Arg Ala Asn Leu Leu Gln Glu Lys Ile Gly Ser Gln Glu Asn
                405                 410                 415
Ser Val Lys Gln Glu Asn Tyr Ser Lys Asn Pro Gln Leu Arg His Gln
            420                 425                 430
Leu Thr Ser Arg Ser Arg Ser Phe Ile His Pro Ala Asn Glu Tyr
        435                 440                 445
Leu Lys Asn Thr Phe Gly Asn Ser His Ser Asn Asp Ile Gly Lys Gly
        450                 455                 460
Val Glu Val Leu Ser Leu Thr Pro Ser Phe Met Asp Ile Pro Glu Lys
465                 470                 475                 480
Glu Arg Glu Thr Glu Arg Ser Pro Ser Ser Asn Tyr Ile Thr Asp Arg
                485                 490                 495
Pro Phe Thr Arg Lys Pro Arg Ser Ser Ser Ile Asp Val Asn His Arg
            500                 505                 510
```

```
Tyr Pro Pro Met Ala Pro Thr Thr Val Ala Thr Ser Pro Gly Ala Leu
            515                 520                 525

Asn Asn Ala Val Ala Ser Asn Leu Asp Asp Gln Leu Ser Leu Thr Ser
        530                 535                 540

Leu Asn Ser Gln Pro Ser Ser Ile Ala Asn Met Met Met Asp Pro Ser
545                 550                 555                 560

Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Asn Val Pro Asp Glu Met Asn Gln Met Phe Ser Pro Pro
    610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
                645                 650                 655

Arg Asn Asp Leu Pro Asp Thr Ser Pro Met Ser Ser Ile Gln Thr Ala
            660                 665                 670

Ser Pro Pro Ser Gln Leu Leu Thr Asp Gln Gly Phe Ala Asp Leu Asp
        675                 680                 685

Asn Phe Met Ser Ser Leu
        690

<210> SEQ ID NO 3
<211> LENGTH: 939
<212> TYPE: DNA
<213> ORGANISM: Saccharomyces cerevisiae
<220> FEATURE:
<221> NAME/KEY: CDS
<222> LOCATION: (1)..(939)
<223> OTHER INFORMATION: PHO13

<400> SEQUENCE: 3 atg act gct caa caa ggt gta cca ata aag ata acc aat aag gag att      48
Met Thr Ala Gln Gln Gly Val Pro Ile Lys Ile Thr Asn Lys Glu Ile
1               5                   10                  15 gct caa gaa ttc ttg gac aaa tat gac acg ttt ctg ttc gat tgt gat      96
Ala Gln Glu Phe Leu Asp Lys Tyr Asp Thr Phe Leu Phe Asp Cys Asp
                20                  25                  30 ggt gta tta tgg tta ggt tct caa gca tta cca tac acc ctg gaa att     144
Gly Val Leu Trp Leu Gly Ser Gln Ala Leu Pro Tyr Thr Leu Glu Ile
            35                  40                  45 cta aac ctt ttg aag caa ttg ggc aaa caa ctg atc ttc gtt acg aat     192
Leu Asn Leu Leu Lys Gln Leu Gly Lys Gln Leu Ile Phe Val Thr Asn
        50                  55                  60 aac tct acc aag tcc cgt tta gca tac acg aaa aag ttt gct tcg ttt     240
Asn Ser Thr Lys Ser Arg Leu Ala Tyr Thr Lys Lys Phe Ala Ser Phe
65                  70                  75                  80 ggt att gat gtc aaa gaa gaa cag att ttc acc tct ggt tat gcg tca     288
Gly Ile Asp Val Lys Glu Glu Gln Ile Phe Thr Ser Gly Tyr Ala Ser
                85                  90                  95 gct gtt tat att cgt gac ttt ctg aaa ttg cag cct ggc aaa gat aag     336
Ala Val Tyr Ile Arg Asp Phe Leu Lys Leu Gln Pro Gly Lys Asp Lys
                100                 105                 110 gta tgg gta ttt gga gaa agc ggt att ggt gaa gaa ttg aaa cta atg     384
Val Trp Val Phe Gly Glu Ser Gly Ile Gly Glu Glu Leu Lys Leu Met
            115                 120                 125
```

```
ggg tac gaa tct cta gga ggt gcc gat tcc aga ttg gat acg ccg ttc      432
Gly Tyr Glu Ser Leu Gly Gly Ala Asp Ser Arg Leu Asp Thr Pro Phe
    130                 135                 140 gat gca gct aaa tca cca ttt ttg gtg aac ggc ctt gat aag gat gtt      480
Asp Ala Ala Lys Ser Pro Phe Leu Val Asn Gly Leu Asp Lys Asp Val
145                 150                 155                 160 agt tgt gtt att gct ggg tta gac acg aag gta aat tac cac cgt ttg      528
Ser Cys Val Ile Ala Gly Leu Asp Thr Lys Val Asn Tyr His Arg Leu
                165                 170                 175 gct gtt aca ctg cag tat ttg cag aag gat tct gtt cac ttt gtt ggt      576
Ala Val Thr Leu Gln Tyr Leu Gln Lys Asp Ser Val His Phe Val Gly
            180                 185                 190 aca aat gtt gat tct act ttc ccg caa aag ggt tat aca ttt ccc ggt      624
Thr Asn Val Asp Ser Thr Phe Pro Gln Lys Gly Tyr Thr Phe Pro Gly
        195                 200                 205 gca ggc tcc atg att gaa tca ttg gca ttc tca tct aat agg agg cca      672
Ala Gly Ser Met Ile Glu Ser Leu Ala Phe Ser Ser Asn Arg Arg Pro
    210                 215                 220 tcg tac tgt ggt aag cca aat caa aat atg cta aac agc att ata tcg      720
Ser Tyr Cys Gly Lys Pro Asn Gln Asn Met Leu Asn Ser Ile Ile Ser
225                 230                 235                 240 gca ttc aac ctg gat aga tca aag tgc tgt atg gtt ggt gac aga tta      768
Ala Phe Asn Leu Asp Arg Ser Lys Cys Cys Met Val Gly Asp Arg Leu
                245                 250                 255 aac acc gat atg aaa ttc ggt gtt gaa ggt ggg tta ggt ggc aca cta      816
Asn Thr Asp Met Lys Phe Gly Val Glu Gly Gly Leu Gly Gly Thr Leu
            260                 265                 270 ctc gtt ttg agt ggt att gaa acc gaa gag aga gcc ttg aag att tcg      864
Leu Val Leu Ser Gly Ile Glu Thr Glu Glu Arg Ala Leu Lys Ile Ser
        275                 280                 285 cac gat tat cca aga cct aaa ttt tac att gat aaa ctt ggt gac atc      912
His Asp Tyr Pro Arg Pro Lys Phe Tyr Ile Asp Lys Leu Gly Asp Ile
    290                 295                 300 tac acc tta acc aat aat gag tta tag                                   939
Tyr Thr Leu Thr Asn Asn Glu Leu
305                 310
```

<210> SEQ ID NO 4
<211> LENGTH: 312
<212> TYPE: PRT
<213> ORGANISM: Saccharomyces cerevisiae

<400> SEQUENCE: 4

```
Met Thr Ala Gln Gln Gly Val Pro Ile Lys Ile Thr Asn Lys Glu Ile
1               5                   10                  15

Ala Gln Glu Phe Leu Asp Lys Tyr Asp Thr Phe Leu Phe Asp Cys Asp
            20                  25                  30

Gly Val Leu Trp Leu Gly Ser Gln Ala Leu Pro Tyr Thr Leu Glu Ile
        35                  40                  45

Leu Asn Leu Leu Lys Gln Leu Gly Lys Gln Leu Ile Phe Val Thr Asn
    50                  55                  60

Asn Ser Thr Lys Ser Arg Leu Ala Tyr Thr Lys Lys Phe Ala Ser Phe
65                  70                  75                  80

Gly Ile Asp Val Lys Glu Glu Gln Ile Phe Thr Ser Gly Tyr Ala Ser
                85                  90                  95

Ala Val Tyr Ile Arg Asp Phe Leu Lys Leu Gln Pro Gly Lys Asp Lys
            100                 105                 110

Val Trp Val Phe Gly Glu Ser Gly Ile Gly Glu Glu Leu Lys Leu Met
```

```
                    115                 120                 125
Gly Tyr Glu Ser Leu Gly Gly Ala Asp Ser Arg Leu Asp Thr Pro Phe
    130                 135                 140

Asp Ala Ala Lys Ser Pro Phe Leu Val Asn Gly Leu Asp Lys Asp Val
145                 150                 155                 160

Ser Cys Val Ile Ala Gly Leu Asp Thr Lys Val Asn Tyr His Arg Leu
                165                 170                 175

Ala Val Thr Leu Gln Tyr Leu Gln Lys Asp Ser Val His Phe Val Gly
                180                 185                 190

Thr Asn Val Asp Ser Thr Phe Pro Gln Lys Gly Tyr Thr Phe Pro Gly
        195                 200                 205

Ala Gly Ser Met Ile Glu Ser Leu Ala Phe Ser Ser Asn Arg Arg Pro
    210                 215                 220

Ser Tyr Cys Gly Lys Pro Asn Gln Asn Met Leu Asn Ser Ile Ile Ser
225                 230                 235                 240

Ala Phe Asn Leu Asp Arg Ser Lys Cys Cys Met Val Gly Asp Arg Leu
                245                 250                 255

Asn Thr Asp Met Lys Phe Gly Val Glu Gly Gly Leu Gly Gly Thr Leu
                260                 265                 270

Leu Val Leu Ser Gly Ile Glu Thr Glu Glu Arg Ala Leu Lys Ile Ser
            275                 280                 285

His Asp Tyr Pro Arg Pro Lys Phe Tyr Ile Asp Lys Leu Gly Asp Ile
        290                 295                 300

Tyr Thr Leu Thr Asn Asn Glu Leu
305                 310

<210> SEQ ID NO 5
<211> LENGTH: 30
<212> TYPE: DNA
<213> ORGANISM: Artificial
<220> FEATURE:
<223> OTHER INFORMATION: Primer Haa1-F

<400> SEQUENCE: 5
gtcgacatgg tcttgataaa tggcataaag                                   30

<210> SEQ ID NO 6
<211> LENGTH: 33
<212> TYPE: DNA
<213> ORGANISM: Artificial
<220> FEATURE:
<223> OTHER INFORMATION: Primer Haa1-R

<400> SEQUENCE: 6
gcggccgctc ataacgaaga catgaaatta tcc                               33
```